United States Patent [19]

Kessler et al.

[11] Patent Number: 4,937,072

[45] Date of Patent: Jun. 26, 1990

[54] IN SITU SPORICIDAL DISINFECTANT

[76] Inventors: Jack H. Kessler, 335 Montclair Ave., Glen Ellyn, Ill. 60137; Robert S. Rosenbaum, 69 Grayfield Ave., West Roxbury, Mass. 02132

[21] Appl. No.: 268,651

[22] Filed: Nov. 7, 1988

Related U.S. Application Data

[63] Continuation of Ser. No. 861,926, May 12, 1986, abandoned.

[51] Int. Cl.$^5$ .................... A61K 37/50; A61K 33/40; A61K 33/18; A61L 2/16

[52] U.S. Cl. .................... 424/94.4; 424/613; 424/614; 424/615; 424/616; 424/669; 424/670; 424/671; 422/29

[58] Field of Search ........ 424/130, 150, 613, 614–616, 424/669, 670, 671, 94.4; 422/29; 435/28

[56] References Cited

U.S. PATENT DOCUMENTS

| | | | |
|---|---|---|---|
| 2,425,285 | 8/1947 | Strickler | 424/130 |
| 3,248,281 | 4/1966 | Goodenough | 424/130 |
| 3,751,562 | 2/1973 | Nichols | 424/150 |
| 4,473,550 | 9/1984 | Rosenbaum et al. | 424/94.4 |
| 4,476,108 | 10/1984 | Kessler et al. | 424/50 |
| 4,564,519 | 1/1986 | Pellico et al. | 424/94.4 |
| 4,576,817 | 3/1986 | Montgomery et al. | 424/94.4 |
| 4,588,586 | 5/1986 | Kessler et al. | 424/94.4 |

FOREIGN PATENT DOCUMENTS

| | | | |
|---|---|---|---|
| 2904217 | 8/1980 | Fed. Rep. of Germany | 424/130 |
| 659698 | 10/1951 | United Kingdom | 424/130 |

OTHER PUBLICATIONS

Thomas et al., Antimicrob. Agents Chemo. (6–78), pp. 1000–1005.

Chung et al., cited in Chem. Abstracts, vol. 91:106857d, 1979.

*Primary Examiner*—Jacqueline Stone
*Attorney, Agent, or Firm*—E. Lieberstein

[57] ABSTRACT

The method comprises forming a sporocide having a defined period of sporocidal activity comprising three components including a peroxide or peroxide generating material, a peroxidase and a salt of iodide which serves as a donor molecule; storing the three components in a nonreacting state to maintain the sporocide in an inactive state and admixing the three components in a aqueous based carrier to cause a catalyzed reaction by said peroxidase for generating free radicals and/or byproducts from the iodide salt (donor molecule) and contacting the surface or object to be sterilized with the activated mixture. The concentration level of the three components can be selected such that an active sporocidal state is maintained for any desired period of time.

13 Claims, No Drawings

IN SITU SPORICIDAL DISINFECTANT

This application is a continuation of prior U.S. application Ser. No. 861,926 Filing Date May 12 1986 now abandoned.

This invention relates to a method of forming an in-situ sporicidal disinfectant in an aqueous based medium.

BACKGROUND

Spores are known to form from aerobic Bacilli, anaerobic Clostridia, selected sarcinae and a few actinomycetes. Spores resemble certain plant seeds in that they do not carry out any metabolic reactions. In this regard they are especially suited to withstand severe environmental stress and are known to survive prolonged exposures to heat, drying, radiation and toxic chemicals. These properties make spores especially difficult to kill in environments, like living tissue or objects which come in contact with living tissue, which would be adversely effected by extreme conditions.

Fungi, viruses and vegetative cells of pathogenic bacteria are sterilized within minutes at 70 degrees centigrade; many spores are sterilized at 100 degrees centigrade. However, the spores of some saprophytes can survive boiling for hours. Heat is presently the most commonly used means to insure sterilization of spores.

The outer coat of spores is made of a keratin-like protein which comprises as much as 80% of the total protein of the spore. It is this protein coat which is responsible for the resistance of spores to chemical sterilizing agents. A variety of compounds have been used to insure sterilization of spores and have found acceptance depending upon constraints imposed by environment and the required efficacy of action. Acids, alkali, phenols, iodophors, salts, heavy metals, chlorine, hypochlorite, alcohols, glutaraldehyde, formaldehyde, ethylene oxide, organic solvents and surfactants all have been shown to have some action as a sterilant. However, of these compounds only aldehydes, ethylene oxide, hypochlorites, and Alcide (EPA Reg. No. 456310-03), are commonly used commercially to kill spores.

Iodine and tincture of iodine, a 2–7% solution of iodine in aqueous alcohol containing KI is known to kill bacteria but not known to be generally effective against spores. Additionally, this mixture has a painful and destructive effect on living tissue. Hydrogen peroxide has been and is widely used as an antiseptic but bacteria and spores vary widely in their susceptibility; spores in particular require high concentrations of hydrogen peroxide (3% and up) and long periods (hours, days) of contact with hydrogen peroxide to insure good killing efficacy.

Hydrogen peroxide is known to dissociate into free radicals. The rate at which free radical species are generated from the decomposition of hydrogen peroxide is believed in accordance with the present invention to determine the sporocidal efficacy of this compound. Enzyme catalyzed reactions are known to occur 10 to 15 orders of magnitude more rapidly than the corresponding non-enzymatic reactions. In accordance with the present invention an enzyme, peroxidase, has been selected to catalyze the reduction of hydrogen peroxide for generating free radicals from iodide which has been added to an aqueous based medium in the form of one of its salts.

The enzyme peroxidase catalyzes the transfer of electrons from iodide to hydrogen peroxide. When an electron is removed from an iodide anion this molecule is transformed into a free radical; this free radical or a by-product of this molecule is the sporocidal entity. The free radicals generated in this process are generated at greatly elevated rates relative to the rate at which free radicals are generated from the non-enzymatic dissociation of peroxide.

Peroxidases are classified as enzymes which act to reduce hydrogen peroxide. The different types of peroxidases are distinguished by the donor molecules they use; donor molecules supply electrons which peroxidase donates to hydrogen peroxide. In accordance with the present invention a peroxidase is used to generate free radicals from iodide. Iodide is capable of acting as a substrate for horseradish peroxidase in the reduction of hydrogen peroxide.

The method of the present invention teaches a practical means to control the generation of free radical species to form a sporocide having a defined period of sporocidal activity. The sporocide of the present invention is formed by combining three components, viz., a peroxide or peroxide generating material, a peroxidase and a source of iodide . . . i.e. an iodide salt. The in-situ sporocidal disinfectant will continuously generate free radicals over a defined period of time depending upon the concentration level of each component in the sporocide.

The duration of peroxide reduction and the amount of sporocidal entities produced can be controlled by careful formulation of the three components comprising the system. As long as the enzymatic reduction of hydrogen peroxide continues, free radicals will be generated. The free radicals being generated have an extremely short lifetime and as such must be continuously generated to prolong the period of sporocidal activity. The duration of the reaction, and therefore its sporocidal lifetime, is controlled via the formulation. Other factors remaining constant, the longer the reaction occurs the greater the sporocidal effectiveness.

The method of the present invention teaches how to maintain the sporocide in a nonreacting state; how to activate the sporocide at the critical moment when sterilization is desired and how to control the generation of free radicals over a preselected time period to complete the sterilization.

The selection of donor molecule is critical to the invention. The use of iodide salts in the sporocide is of paramount importance since the iodide molecules or products thereof are the molecules transformed in the reaction into the sporocidal agents. The instantaneous dissolution rate and very high solubility of iodide salts like sodium iodide and potassium iodide make them ideal candidates for this application. Many salts of iodides may be used either alone or in combination with other iodides. The choice will usually be dictated by cost and manufacturability of the materials chosen.

Any aqueous based medium which does not interfere with the peroxidative catalytic cycle and does not introduce compounds which are capable of reacting with the products or by-products of the peroxidative catalytic cycle is suitable for the practice of this technology. That is, the medium should allow for the catalytic reduction of hydrogen peroxide and the formation of the sporocidal entities normally found in simple buffered solutions like 0.010 molar sodium phosphate, pH 7.0. From the following examples, it will be apparent that the method of the present invention reduces the concentration of spores in solution by log order magnitudes to a final concentration where the count is essentially zero. Accordingly, contacting spores with a sporicide in solution formed in accordance with the present invention will result in sterilizing the solution substantially free of spores.

The present invention incorporates a peroxide or a peroxide generating compound, a peroxidase, and a salt of iodide like sodium or potassium iodide, which are readily available, inexpensive and easily incorporated into a powder or pill format.

SUMMARY OF THE INVENTION

The present invention provides a practical method for producing an in-situ sporocidal disinfectant during a defined time period by subjecting spores to a mixture containing a peroxidase, a peroxide or peroxide generating comopund and a salt of iodide with the components formulated within predetermined concentration levels. The three components of this invention must be stored in a nonreacting state.

According to the invention sporocidal entities are continuously generated in a short time period at an effective concentration by dissolving a combination of a peroxidase, a peroxide generating compound and a salt of iodide in an aqueous based medium. The components of this invention are maintained in a nonreactive state by storing the components in a powdered or pilled form and then activated by admixture in a suitable aqueous based medium for use. The components of this invention are compatible with common dessicants such as silica gel which might be used to prolong the shelf-life of a powered mixture or a pill. A hermetically sealed container could alternately be used to prolong the shelf-life when extended product lifetime is necessary.

DESCRIPTION OF THE PREFERRED EMBODIMENT

The material used as an in-situ sporocidal disinfectant in accordance with the method of this invention is a combination of preselected iodides, a peroxide or peroxide generating compounds and a peroxidase stored in a nonreactive state such as in pill or powder form which can be activated to generate free radicals when combined to permit a catalyzed reaction by said peroxidase preferably by admixture in a suitable aqueous based medium such as a buffered normal saline solution.

The components may be rendered nonreactive by using a lyophilized peroxidase. Any solid entity which liberates upon dissolution a peroxide which is useable by peroxidase can serve as the source of peroxide. Compounds which yield hydrogen peroxide upon dissolution in water or an appropriate aqueous based medium include but are not limited to metal peroxides, percarbonates, persulphates, perphosphates, peroxyacids, alkyperoxides, acylperoxides, peroxyesters, urea peroxide and perborates. Any compound which generates a peroxide that peroxidase can use to oxidize iodides is an acceptable source of peroxide for this invention; this includes a large number of compounds as one skilled in the art will recognize. Mixtures of two or more of these substances can also be used. When this is done, all components can be mixed together and activated by introduction into a aqueous based medium such as a mildly buffered aqueous saline solution or a 5% glycerin, 0.010 molar potassium phosphate solution. This system is compatable numerous different types of buffers which allows for a formulation organoleptically compatible with living tissue of materials which come in contact with living tissue.

The system of this invention incorporates a peroxide as an acceptor molecule. The enzyme peroxidase catalyzes transfer of electrons from iodides to acceptor molecules. When an electron is removed from the iodide, this molecule or a by-product thereof is transformed into a sporocidal entity. A cycle of the enzyme mechanism is illustrated below:

Enzyme + HOOR(peroxide) OR/Enzyme 1 + H2O

OR/Enzyme 1 + I OR/Enzyme 2 + I*

OR/Enzyme 2 + I Enzyme + I* HOR where

R=hydrogen, methyl or ethyl

I=iodide anion

I*=free radical of iodide anion

The increased rate of formation of free radicals produced by this chemical system allows for rapid generation of high concentrations of free radicals relative to the non-catalyzed decomposition of hydrogen peroxide.

The preferred peroxidase is horseradish peroxidase which is one of a class of peroxidases identified by the IUB and IUPAC, Enzyme Commission identification No. E.C. 1.11.1.7. Peroxidase can be obtained from a wide variety of sources; although other peroxidases, like myeloperoxidase and lactoperoxidase, can be used the cost is increased and the stability of the final product is reduced. Commercially obtained peroxidase comes lyophilized as a dry powder. Peroxidase, which uses a peroxide as an acceptor molecule, is believed to impart to the sporocidal composition of this invention an enormous catalytic advantage in generating active constituents capable of killing spores in defined areas relative to using only hydrogen peroxide. A high concentration of free radicals are produced in short time periods for example, the reaction rate to form free radicals occurs essentially instantaneously and proceeds at a rate determined by the initial concentration of each of the three critical components of the system and the environment in which the reaction occurs. The peroxidase can come from a variety of sources and can be isolated by any of the well-known prior art procedures as used by the many companies which offer a peroxidase for sale. The use of horseradish peroxidase is preferred since it is easily isolated, has low cost, and has very high stability giving it a long lifetime; however, other sources of peroxidase can be used. Peroxidases have variable substrate specificities depending upon the source from which they are isolated. Hydrogen peroxide is often the most effective substrate.

The iodides are molecules which can be acted upon to aid information of sporocidal free radicals. Many iodides can be use as will be recognized by those skilled in the art. Sodium iodide and potassium are two obvious choices since their cost is low and their solubility characteristics are very suitable. Evidence indicates that high concentrations of organisms may require meaningfully high concentrations of iodide salt (donor molecule); these concentrations will be a high multiple of the dissociation constant for the donor molecule (iodide anion) with peroxidase and be log orders higher than the dissociation constant. It is obvious that for practical applications the rate of dissolution of donor molecule can be critical to successful application of this invention; iodide salts with instantaneous dissolution rates and high solubility are therefore preferred.

A prerequisite for the storage of any preparation is not allowing all three components (iodides, peroxide, and peroxidase) of the system to combine under conditions where the catalytic process can occur. That is, it is imperative that the storage of the components will not allow depletion of the component parts of the system until the reaction is initiated immediately prior to use. If the components are allowed to react before intended for use, the combination of these components under such conditions will precipitate the depletion of the enzyme's substrate molecules and thereby attenuate the effectiveness of the preparation. Any combination of the components of this system (iodides, acceptor molecules, or peroxidase) which precludes the catalytic reaction from occurring is acceptable for storage prior to use. That is, if it is practical to separate any one of the three components from the other two prior to administration, this would serve the purpose of preserving the integrity of the system. Alternately, it is possible to have two separate mixtures which contain any two of the components of the system in any combination and to combine these two mixtures prior to use. The present invention can accomplish this by combining the three components of the invention in a dry form.

The present invention can utilize a concentration of peroxide, preferably hydrogen peroxide above 10 micromolar, with a preferred concentration range between 1 millimolar and 0.001 millimolar. It is remarkable that this invention is effective at peroxide concentrations that are on the order of 10,000 to 100,000 fold less than that found in 3% peroxide solutions. The present invention can utilize concentrations of iodides above 10 micromolar, with a preferred range of 35 micromolar to 100 millimolar. The present invention can utilize a concentration of horseradish peroxidase above 0.00001 mg/ml, with a preferred range of 0.5 to 0.01 mg/ml.

EXAMPLES

1. We determined the killing time for the in-situ sporocidal dinfection system of this invention against spores of *Bacillus pumilus* at 1 million organisms per ml as compared to chlorox bleach(NaOCl) and Sporicidin Lot# LO853 which are known sporicidal agents. This experiment utilized *Bacillus pumilus* spores since it is recognized by one skilled in the art that the ability to kill this organism indicates the ability to kill all other known spores: that is, all other known spores will be susceptible. The reagents used are shown below:
1. Sodium iodide was dissolved at 150 mg in 100 ml of phosphate buffered saline(PBS).
2. 30% hydrogen peroxide was diluted 1 part to 10,000 parts PBS.
3. NaOCl was made 0.85% in PBS.
4. Horse-radish peroxidase was dissolved at 0.5 and 0.05 mg/ml.
5. NaOCl was diluted to 0.5%, oil and 0.01% in water.
6. Sporicidin was used undiluted and diluted 1/16 as per manufacturers instsructions.
7. Organisms were spun down to remove growth media and diluted in PBS to yield 1 million organisms per ml.

The reagents were mixed in the following order in the designated aliquots:
1. PBS: 1.75 ml
2. Organism: 0.50 ml
3. Sodium iodide: 1.75 ml
4. Peroxide: 0.50 ml
5. Peroxidase: 0.05 ml For the various dilutions of NaOCl and Sporicidin, 0.5 ml of the organism was added to 4.5 ml of the sporicide. At 10, 20, 60 minutes and at 24 hours after contamination of the germicides, 1 ml of the product was removed and diluted to STAT broth (trypticase soy broth with 2% tween-20 and 0.5% lecithin). for the NaOCl, 0.1% sodium sulfate was also added and for the Sporicide, the media also was supplemented with 10% serum. The surviving spores were counted via STAT agar pour plates and a surface streak spiral count. All plates were incubated 48 hours at 35 degrees centigrade.
*=indicates exponentiation
D10 was determined using the Stumbo Equation

TABLE 1

Peroxidase at a final concentration of 0.05 mg/ml

| Time | Spore Count | Log 10 | D10 Value |
|---|---|---|---|
| 0 | $3.4 \times 10^{6}$ | 6.53 | |
| 10 min | $1.7 \times 10^{5}$ | 5.23 | 7.7 min |
| 20 min | $5.8 \times 10^{3}$ | 3.76 | 7.2 min |
| 60 min | $2.4 \times 10^{2}$ | 2.38 | 14.5 min |
| 24 hr. | <10 | <1 | |

Average D10 = 9.8 minutes

TABLE 2

Peroxidase at a final concentration of 0.005 mg/ml

| Time | Spore Count | Log 10 | D10 Value |
|---|---|---|---|
| 0 | $3.4 \times 10^{6}$ | 6.53 | |
| 10 min | $4.5 \times 10^{5}$ | 5.65 | 11.4 min |
| 20 min | $3.3 \times 10^{4}$ | 4.52 | 10.0 min |
| 60 min | $9.8 \times 10^{2}$ | 2.99 | 16.9 min |
| 24 hr. | <10 | <1 | |

Average D10 = 12.8 minutes

TABLE 3

0.5% NaOCl

| Time | Count | Log 10 | D10 Value |
|---|---|---|---|
| 0 | $3.4 \times 10^{6}$ | 6.53 | |
| 10 min | <10 | <1 | 1.8 min |
| 20 min | <10 | <1 | |
| 60 min | <10 | <1 | |
| 24 hr. | <10 | <1 | |

Average D10 < 1.8 minutes

TABLE 4

).1% NaOCl

| Time | Count | Log 10 | D10 Value |
|---|---|---|---|
| 0 | $3.4 \times 10^{6}$ | | |
| 10 min | <10 | <1 | 1.8 min |
| 20 min | <10 | <1 | |
| 60 min | <10 | <1 | |
| 24 hr. | <10 | <1 | |

Average D10 < 1.8 minutes

TABLE 5

| | 0.01% NaOCl | | |
|---|---|---|---|
| Time | Count | Log 10 | D10 Value |
| 0 | $3.4 \times 10^6$ | 6.53 | |
| 10 min | <10 | <1 | 1.8 min |
| 20 min | <10 | <1 | |
| 60 min | <10 | <1 | |
| 24 hr. | <10 | <1 | |

Average D10 < 1.8 minutes

TABLE 6

| | Sporicidin (Undiluted) | | |
|---|---|---|---|
| Time | Count | Log 10 | D10 Value |
| 0 | $3.4 \times 10^6$ | 6.53 | |
| 20 min | <10 | <1 | 2.78 min |
| 60 min | <10 | <1 | |
| 24 hr. | <10 | <1 | |

Average D10 < 2.7 minutes

TABLE 7

| | Sporicidin Diluted 1/16 | | |
|---|---|---|---|
| Time | Count | Log 10 | D10 Value |
| 0 | $3.4 \times 10^6$ | 6.53 | |
| 10 min | $1.6 \times 10^6$ | 6.20 | 30.0 min. |
| 20 min | $8.5 \times 10^5$ | 5.93 | 33.3 |
| 60 min | — | — | |
| 24 hr. | <10 | <1 | — |

Average D10 = 31.8 minutes

We claim:

1. A method of killing spores consisting essentially of the steps of: (a) combining three components in an aqueous solution to form a sporicidal disinfectant having a defined period of sporicidal activity with said three components consisting essentially of: a peroxide generating material, a peroxidase selected from the class contained in the E.C. #1.11.1.7 and a salt of iodide; and (b) contacting said spores with said aqueous solution within said defined period of sporicidal activity for killing said spores.

2. A method for sterilizing an aqueous solution to render such solution substantially free of spores consisting essentially of the steps of: forming a sporicide by combining three components including, a peroxide, a peroxidase selected from the class contained in the E.C. #1.11.17 and a salt of iodide; storing said three components in a nonreacting state and admixing the three components in said aqueous solution to initiate sporicidal activity by causing a catalyzed reaction which forms sporicidal entities by removing electrons from the iodide molecules.

3. A method as defined in claim 2 wherein said components are stored in a dry form such as a powder or in a pill needing only to be dissolved in an aqueous based medium to be activated.

4. A method as defined in claim 2 wherein said salt of iodide is sodium iodide.

5. A method as defined in claim 4 wherein the concentration of said iodide in solution lies in a range of between 35 micromolar and 100 millimolar.

6. A method as defined in claim 4 wherein said peroxide generating material is selected from the class consisting of metal peroxides, percarbonates, persulphates, perphosphates, peroxyacids, alkyperoxides, acylperoxides, peroxyesters, urea peroxide and perborates.

7. A method as defined in claim 6 wherein said peroxide concentration has a minimum concentration of 10 micromolar.

8. A method as defined in claim 6 wherein said source of peroxidase is horseradish peroxidase.

9. A method as defined in claim 8 wherein the minimum concentration of said peroxidase is 0.00001 mg/ml.

10. A method as defined in claim 8 wherein said salt of iodide is potassium iodide.

11. A method as defined in claim 10 wherein said aqueous based medium comprises water or a solution containing water.

12. A method as defined in claim 11 wherein said aqueous based medium is a saline solution.

13. A method as defined in claim 10 wherein said source of peroxide is sodium perborate.

* * * * *